(12) United States Patent
Viens et al.

(10) Patent No.: US 8,117,898 B2
(45) Date of Patent: Feb. 21, 2012

(54) METHOD FOR SENSING GAS COMPOSITION AND PRESSURE

(75) Inventors: Jean François Viens, Québec (CA); Loïc Le Noc, Québec (CA)

(73) Assignee: Institut National D'Optique, Sainte-Foy, Quebec (CA)

( * ) Notice: Subject to any disclaimer, the term of this patent is extended or adjusted under 35 U.S.C. 154(b) by 679 days.

(21) Appl. No.: 12/340,238

(22) Filed: Dec. 19, 2008

(65) Prior Publication Data

US 2010/0154510 A1    Jun. 24, 2010

(51) Int. Cl.
     *G01L 21/12*      (2006.01)
     *G01N 25/18*      (2006.01)

(52) U.S. Cl. ..................... 73/31.04; 73/25.03; 73/755

(58) Field of Classification Search .................. 73/25.03, 73/31.04, 557

See application file for complete search history.

(56) References Cited

U.S. PATENT DOCUMENTS

| | | | |
|---|---|---|---|
| 4,580,439 A * | 4/1986 | Manaka | 73/31.06 |
| 6,945,119 B2 | 9/2005 | Bills et al. | |
| 7,331,237 B2 | 2/2008 | Borenstein | |
| 7,456,633 B2 | 11/2008 | Hong et al. | |
| 7,541,587 B2 * | 6/2009 | Cutler et al. | 250/339.13 |
| 2003/0041670 A1 | 3/2003 | Hirota et al. | |
| 2006/0021444 A1 | 2/2006 | Borenstein | |
| 2007/0069133 A1 | 3/2007 | DeWames et al. | |

* cited by examiner

*Primary Examiner* — Lisa Caputo
*Assistant Examiner* — Punam Roy
(74) *Attorney, Agent, or Firm* — Merchant & Gould P.C.

(57) ABSTRACT

A method for sensing gas composition and gas pressure, based on the thermal constants of a variable electrical resistor, is presented. The method for sensing gas composition and pressure includes monitoring a variable electrical resistor whose dynamic thermal response is determined by the thermal conductivity and thermal capacity of the surrounding gas of a given atmospheric environment. In the thermal domain, the sensor has a low-pass characteristic, whose phase delay is determined by the thermodynamic characteristics of the surrounding gas such as composition and pressure. The method can be used for sensing gas composition and can also be used for sensing gas pressure.

28 Claims, 5 Drawing Sheets

METHOD FOR SENSING GAS COMPOSITION AND PRESSURE

FIELD OF THE INVENTION

The present invention is directed to a method and apparatus for sensing gas composition or pressure or both.

BACKGROUND OF THE INVENTION

A conventional sensor, such as a Pirani gauge, is calibrated against several known pressures to determine a relationship between ambient pressure and power dissipated by the sensor. On one hand, since a Pirani gauge may be designed to have a wide dynamic range and be relatively simple and inexpensive, there is a need to be able to use this type of pressure gauge as a substitute for much higher priced gauges such as capacitance manometers and ionization gauges. On a second hand, the growing markets of high-performance wafer-level micro-packaging require miniaturization of the pressure sensors and integration to standard CMOS processes and MEMS micro-devices such as bolometers, gyroscopes and accelerometers. In addition, these markets may require the capability of the sensor for measuring both the gas composition and the gas pressure.

Pressure sensors based on MEMS micro-sensor devices can achieve both low-cost and CMOS-compatible integration. However, existing MEMS micro-sensor devices may show inaccurate pressure readings when subjected to temperature fluctuations, especially at low pressures. US 2007/0069133 A1 relates to such temperature-sensitive micro-bolometer sensor, whereas the electrical response of the sensor depends on the substrate and environment temperatures by virtue of the temperature dependency of the variable resistance. Furthermore, the method for pressure measurement relies on an absolute voltage reading instead of differential voltage readings, wherein absolute voltage reading may be subjected to inaccuracies if fabrication errors occur from one sensor to the other. The method described in this prior art does not provide gas composition measurements.

Pressure micro-sensors showing relative immunity to temperature fluctuations have been developed. U.S. Pat. Nos. 6,945,119 B2 and 7,331,237 B2 relate to pressure sensors integrated in a CMOS circuit. Temperature fluctuation compensation is achieved using a combination of temperature-sensitive and temperature-insensitive elements coupled to a bridge readout circuit. However, temperature compensation of the gauges is achieved at the cost of structural complexity of the device and readout circuit, which impede integration of such sensors into MEMS micro-devices. Furthermore, the method for pressure measurement relies on an absolute voltage reading instead of differential voltage readings which lead to inaccuracies if fabrication errors occur from one gauge to the other. The methods described in these prior arts do not provide gas composition measurements.

An apparatus and method for measuring both the gas composition and the gas pressure is disclosed in U.S. Pat. No. 7,456,633. This disclosure relates to an apparatus comprising a vacuum container, a pressure container, a discharge container, an ion gauge and a residual gas analyzer; arranged in such a way that miniaturization becomes very difficult and integration to standard CMOS processes and to MEMS micro-device is not achievable in practice.

It is therefore the object of the present invention to provide an apparatus and method allowing 1) miniaturization of the wide-dynamic-range sensors to address the high-performance micro-packaging markets and 2) integration to standard CMOS processes and MEMS micro-devices such as bolometers, gyroscopes and accelerometers, 3) relative immunity of the sensor to temperature fluctuations, and 4) capability for real-time gas pressure and/or gas composition measurements.

SUMMARY OF THE INVENTION

The invention presents a novel method for measuring gas composition or gas pressure of a given atmospheric environment. The gas sensor and method of operation herein described in this invention disclosure provides real-time gas composition or gas pressure measurements over a large dynamic range. The gas sensor and method of operation are compatible with standard CMOS fabrication processes and readout circuits.

The method for sensing gas composition and gas pressure is based on the thermal constants of a variable electrical resistor. The method consists of monitoring the variable electrical resistor whose dynamic thermal response is determined by the thermal conductivity and thermal capacity of the surrounding gas of a given atmospheric environment. The gas sensor and method of operation herein described in this invention disclosure comprises a variable electrical resistor and a readout circuit for driving the electrical voltage across the variable resistor. When the variable resistor is electrically excited and heated by the readout circuit, its temperature at equilibrium is a function of applied electrical power and of thermal transfer to the environment and to the surrounding gas. The method for gas sensing consists of heating the variable resistor with modulated electrical excitations, at a given modulation frequency, and of measuring its dynamic thermal response. In the thermal domain, the resistor has a low-pass characteristic, whose phase delay is determined by the thermodynamic characteristics of the surrounding gas such as composition and pressure. Specifically, the method consists of measuring the phase delay between the modulated excitation and the thermal response of the variable resistor. The phase delay provides a measurement of the thermal capacity and thermal conductivity of the surrounding gas, both being related to gas composition and gas pressure.

Thus, in accordance with an aspect of the invention, there is provided a method for sensing gas consisting of:
  providing a variable electrical resistor in a gas environment, said variable electrical resistor changing electrical resistance with a change of temperature;
  electrically exciting said variable electrical resistor with a periodically modulated voltage source signal;
  measuring a time delay between the signal modulation of said periodically modulated voltage source and the signal modulation of said variable electrical resistor; and
  determining gas pressure from said time delay; or
  determining gas composition from said time delay, said gas pressure or said gas composition being determined from a mathematical parameter relation.

In accordance with another aspect of the invention, there is provided a gas sensor assembly comprising:
  at least one variable electrical resistor proximal to a substrate, exposed to the gas pressure of a given atmospheric environment;
  an electrical readout circuit connected to said variable electrical resistor, said variable electrical resistor acting as a variable electrical resistance in said electrical readout circuit;
  a periodically modulated voltage source electrically connected to said variable electrical resistor, wherein said periodically modulated voltage source is part of said readout electrical circuit; and a passband filter electrically connected to a phase comparator.

These and other features and advantages of the invention will be apparent to those skilled in the art from the following detailed description of preferred embodiments, taken together with the accompanying drawings.

DETAILED DESCRIPTION OF THE INVENTION

The invention presents a novel method for measuring gas composition or gas pressure of a given atmospheric environment. The gas sensor and method of operation herein described in this invention disclosure provides real-time gas composition or gas pressure measurements over a large dynamic range. The gas sensor and method of operation are compatible to standard CMOS fabrication processes and readout circuits.

Figure 1:
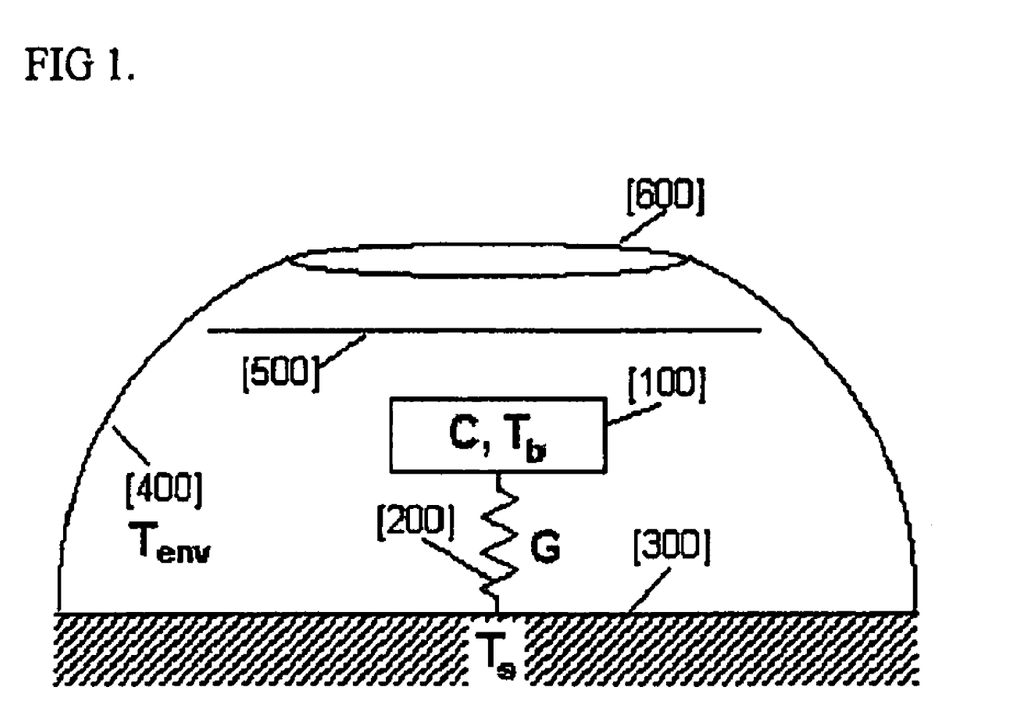
FIG. 1. is a schematic representation of the gas sensor device and its surroundings.

FIG. 1 schematizes an exemplary embodiment of the gas sensor. The gas pressure sensing element consists of a variable electrical resistor [100], whose electrical resistance changes with respect to a change of its temperature. The variable electrical resistor [100] is suspended in close proximity to a substrate [300] through suspending legs [200]. The variable electrical resistor [100] may consist of a suspended micro-thermistor, a suspended micro-electro-mechanical (MEMS) element, a suspended micro-bolometer platform, a suspended micro-wire, a suspended coil, or any variable electrical resistor device proximal to a substrate [300] and connected to the said substrate by suspending legs [200]. The variable electrical resistor [100] may have a width between 0.1 μm and 1000 μm, a length between 0.1 μm and 1000 μm, and a thickness of up to 10 μm. The suspending legs [200] must provide enough mechanical rigidity for suspending the variable electrical resistor [100] at least 0.1 μm above the substrate [300]. Standard CMOS fabrication processes, or MEMS fabrication processes, can be used to fabricate the suspended electrical resistor device on the substrate. The suspending legs [200] may be made of silicon nitride or silicon dioxide materials, and have a length between 1 μm and 1000 μm. The suspending legs [200] should have smaller widths than the variable electrical resistor [100] in order to procure thermal isolation of the variable resistor [100] from the substrate [300] and to provide a path for electrical connection to the substrate [300]. The substrate [300] may consist of a silicon wafer or a CMOS electrical readout circuit or any CMOS integrated device. The substrate is partly or fully enclosed within a gas pressure environment [400] which may include a window [500] (e.g. infrared window or diaphragm or mask) for shielding the variable resistor [100] from excess infrared radiation coming from the environment [400], and may include an optical aperture [600] for providing the variable resistor [100] infrared radiation from a scene. The environment [400] must be large enough to entirely encapsulate the variable electrical resistor [100] and suspending legs [200]. Since the variable electrical resistor [100] and suspending legs [200] have micrometer-scale dimensions, the environment [400] encompassing the variable resistor may have a volume as small as 1 picoliter ($10^{-15}$ m$^3$). The environment [400] is filled with a gas that exerts pressure equally everywhere in the environment, including the top and bottom surfaces of the variable electrical resistor [100]. The gas may be composed of air, oxygen, nitrogen, noble gas or a mixture of several different gases including water vapor, carbon dioxide, nitrogen dioxide or any other trace gases or pollutant gases.

Figure 2:
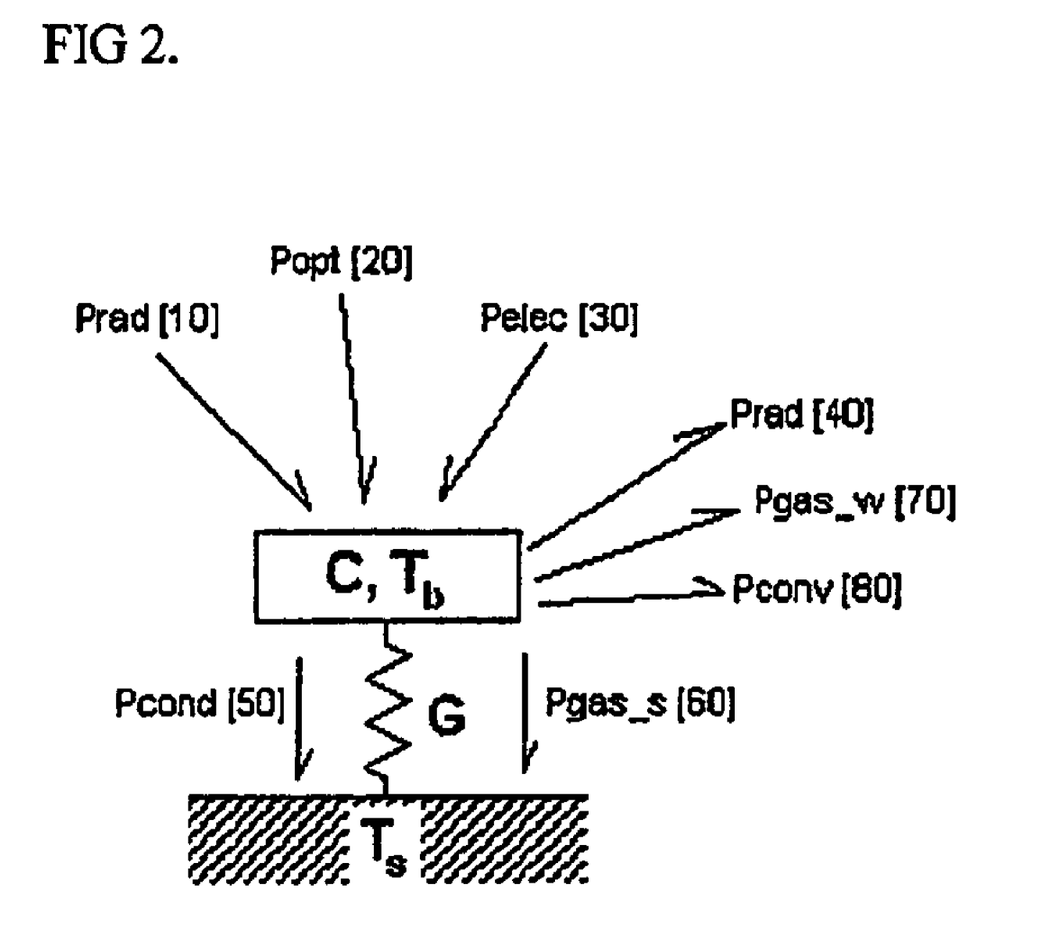
FIG. 2. shows the total heat budget of the system defined as the thermal transfers between the variable electrical resistor and the substrate and environment.

The temperature of the variable electrical resistor [100] is a function of applied heating power and thermal transfers to the substrate and to the environment. FIG. 2 shows the total heat budget of the system defined as the thermal transfers between the variable electrical resistor [100] and the substrate [300] and environment [400]. Specifically, the variable electrical resistor [100] receives heat from a plurality of sources:

$P_{rad,e}$, by absorbing infrared radiation emitted by the environment [10].

$P_{opt}$, by absorbing infrared radiation coming from the scene through the window [20]

$P_{elec}$, by Joule heating when an electrical current is applied from the legs through the variable electrical resistor [30].

And the variable electrical resistor [100] dissipates heat to a plurality of thermal conduction paths:

$P_{rad}$, by thermal radiation [40]

$P_{cond}$, by thermal conduction to the substrate through the legs [50]

$P_{gaz,s}$, by thermal conduction to the substrate through the gas [60]

$P_{gaz,w}$, by thermal conduction to the window through the gas [70]

$P_{conv}$, by thermal convection to the window through the gas [80]

The heat budget is the sum of all inward and outward power components of the variable electrical resistor [100], as shown in FIG. 2. The main component to the heat budget, the electrical excitation $P_{elec}$ [30], is related to the electrical resistance $R_b$ of the variable resistor [100], the electrical potential $V_b$ across the legs [200] of the resistor, and the electrical current $i_b$ applied through the resistor.

The variable electrical resistor [100] may comprise a plurality of materials or a plurality of thin film materials surrounded by gas. The heat capacity C of the variable electrical resistor [100] can be expressed as a combination of resistor heat capacity $C_{resistor}$ and gas heat capacity $C_{gas}$:

$$C=C_{resistor}+C_{gas}=(V_1\rho_1 c_1+V_2\rho_2 c_2+\ldots)+V_{gas}\rho_{gas}c_{gas}$$

Where V is the volume of each of the resistor materials, ρ is the density of each of the resistor materials and c is the mass specific heat of each of the resistor materials. $C_{gas}$ is the effective heat capacity of the gas surrounding the variable resistor [100] and is dependent on the density $\rho_{gas}$ of the gas, the mass specific heat $c_{gas}$ of the gas and the effective volume $V_{gas}$ of the gas surrounding the variable resistor. The effective heat capacity $C_{gas}$ of the gas surrounding the variable resistor is therefore dependent on the gas composition and pressure ρ by virtue of the ideal gas law:

$$C=C_{resistor}+V_{gas}(pM/RT)c_{gas}=C_1+C_2 p$$

Where $C_1=C_{resistor}$ and $C_2=MV_{gas}c_{gas}/RT$.

In one embodiment, the variable electrical resistor [100] comprises a combination of silicon dioxide and silicon nitride thin films for procuring mechanical rigidity to the resistor; a metallic thin film for procuring electrical conductivity to the resistor; and a thermally sensitive thin film material for procuring change of electrical properties with a change of temperature of the resistor. The thermally sensitive thin film material may consist of vanadium oxide, titanium oxide or amorphous silicon. Vanadium oxide (such as $VO_x$ with $1<x<3$) has received most attention as a variable electrical resistor material because of the large temperature coefficient of resistance (TCR) of about 2% per Kelvin near 20° C. The properties of vanadium oxide films are dependent of the microstructure and crystallinity. These can be controlled by the experimental process parameters, such as the molecular precursors, heat treatments and controlled atmosphere. Other thermally sensitive membrane materials can be used for the variable electrical resistor [100] ideally with a temperature coefficient of resistance (TCR) of at least 0.5% per Kelvin. The thermally sensitive membrane material is not limited to a specific material composition; it may consist of vanadium oxide, titanium oxide, amorphous silicon or any material with a temperature coefficient of resistance (TCR) of at least 0.5% per Kelvin.

The coefficient of thermal conduction G between the variable electrical resistor [100] and its surroundings [300] [400] can be described by the contribution of several thermal dissipation mechanisms of the system [40] [50] [60] [70] [80]:

$$G=G_{leg}+G_{radiation}+G_{gas}+G_{conv}+\ldots$$

where $G_{leg}$ is the coefficient of thermal conduction between the variable electrical resistor [100] and the substrate [300] through the suspending legs [200] which determines the heat dissipation through the legs [50]. This coefficient depends on the leg length, leg cross-section and leg material. The typical thermal conductivity to the substrate through the legs is less than $10^{-6}$ W/K.

$G_{radiation}$ is the coefficient of thermal conduction between the variable electrical resistor [100] and the environment [400] by emitted infrared radiation which determines the heat dissipation through radiation [40]. This coefficient depends on the surface area of the variable electrical resistor [100] and on its spectral emissivity which could be a blackbody or non-blackbody function of temperature. For an ideal blackbody material, this coefficient of thermal conduction can be approximated as the sum of radiated power from the resistor bottom surface facing the substrate [300] and from the resistor top surface facing the environment [400]:

$$G_{radiation}=\sigma\epsilon\beta A(T_b^4-T_s^4)/(T_b-T_s)+\sigma\epsilon\beta A(T_b^4-T_{env}^4)/(T_b-T_s)\approx 4\sigma\epsilon\beta A(T_s^3+T_{env}^3)$$

where $\sigma$ is the Stefan-Boltzmann constant, $\epsilon$ is the effective emissivity of the variable electrical resistor [100], A is its surface area, $\beta$ is a form factor that includes thermal dissipation through other parts of the resistor structure, $T_b$ is the resistor temperature, $T_s$ is the substrate temperature and $T_{env}$ is an effective environment temperature related to the hemispheric distribution of all thermal components of the environment seen by the variable electrical resistor [100]. The right-hand side of the equation assumes that the temperature difference between the resistor and the substrate is small with respect to the absolute temperature of the resistor ($|T_b-T_s|<<T_b$) which is valid to 1% error when the resistor is heated only by a few degrees Kelvin.

$G_{gas}$ is the coefficient of thermal conduction between the variable electrical resistor [100] and its surroundings through the gas, which comprises heat dissipation to the substrate [300] through the gas [60] and heat dissipation to the environment [400] through the gas [70]. This coefficient can be obtained by the kinetic theory of gases. The heat conduction $G_{gas}(p)$ of a platform, a wire or a coil follows similar mathematical form with respect to pressure p. In the case of the heat conduction between a platform and a substrate the mathematical form is the following;

$$G_{gas}=\frac{\beta\cdot A}{\frac{ds}{\lambda_{gas_s}}+\frac{1}{\gamma_{gas}\cdot p}}+\frac{k\cdot\beta\cdot A}{\frac{de}{\lambda_{gas_e}}+\frac{1}{\gamma_{gas}\cdot p}}$$

Where p is the gas pressure, $d_s$ the distance between the variable electrical resistor [100] and the substrate [300], $d_e$ the distance between the variable electrical resistor [100] and the window [500], A is the surface area of the variable electrical resistor [100], $\beta$ is a form factor that includes thermal dissipation through other parts of the resistor structure, and $k=(T_b-T_{env})/(T_b-T_s)$. In the absence of window [500], $d_e$ can be defined as an effective distance between the variable electrical resistor [100] and the environment [400]. $\lambda_{gas}$ is the thermal conductivity of the gas in the high-pressure regime and $\lambda_{gas}$ is the thermal conductivity per unit pressure and length in the low-pressure regime. The $\lambda_{gas}$ conductivity coefficient depends on temperature:

$$\lambda_{gas}=\lambda_o+(d\lambda/dT_s)\cdot(T_g-T_o)$$

Where $T_g$ is an effective gas temperature given by $T_g=(1-\eta)T_x+\eta T_b$, where $T_x=T_s$ (substrate side) or $T_x=T_{env}$ (environment side) and $\eta$ is a thermal distribution factor; typically $\eta\sim 0.5$. For air: $d\lambda/dT=7.2167$e-005 W/mK$^2$ and $\lambda_o$=0.0243 W/mK at $T_o$=273K. Other gases show different coefficients. The coefficient of thermal conduction $G_{gas}$ between the variable electrical resistor [100] and its surroundings [300] [400] through the gas is thus function of gas composition and pressure.

$G_{conv}$ is the coefficient of thermal conduction between the variable electrical resistor [100] and its surroundings by gas convection [80]. The heat transferred by free convection [80] from the variable electrical resistor [100] into the gas to the environment [400] at the temperature $T_{env}$ is given by $$P_{conv}=G_{conv}\cdot\Delta T=Ah(T_b-T_{env})$$

Where h is the convection coefficient of the gas [in air h=5 W/m$^2$K]. In practice, the convection coefficient h is not always known precisely, and the gas pressure measurement method herein described in this invention cancels the need for precise knowledge of this term of the equation. For most cases encompassed within this invention, the thermal conduction $G_{conv}$ by free air convection through gas movement is negligible compared to the thermal conduction $G_{gas}$ through the gas.

The thermal conduction G between the variable electrical resistor [100] and its surroundings [300] [400] can also be described by the contribution from additional factors herein not mentioned, dependent on the resistor three-dimensional design and fabrication. In practice, these additional factors are not always known precisely, and the gas measurement method herein described in this invention cancels the need for precise knowledge of these terms of the equation.

The above description shows that the thermal capacity C and thermal conductivity G of the system are both related to gas composition and gas pressure. Therefore, it is the object of the gas sensor and method of operation herein described in this invention disclosure to provide a measurement of the thermal capacity and thermal conductivity of the system, from which gas composition or gas pressure can be determined.

The variable electrical resistor [100] is electrically excited by a voltage source connected to it. Since the variable electrical resistor device is electrically resistive, it is well known in the art that this electrical excitation procures heating to the resistor by virtue of the Joule effect. The temperature of the variable electrical resistor [100] at equilibrium is a function of applied electrical power [30] and of thermal transfer to the substrate [300] and to the environment [400] via the plurality of thermal dissipation mechanisms previously described [10] [20] [40] [50] [60] [70] and [80]. The principle of gas sensing consists of heating the variable electrical resistor [100] by Joule heating [30] and of measuring dynamically the thermal capacity and thermal conductivity of the system, both being related to gas composition and pressure, and from which gas composition or gas pressure can be determined. Specifically, the method of sensing gas with a variable electrical resistor device is based on probing its thermal response with modulated electrical excitations [30], wherein the thermal response is determined by the thermal capacity and thermal conductivity of the surrounding gas of a given atmospheric environment. In the thermal domain, the variable electrical resistor has a low-pass characteristic, whose phase delay is determined by the thermodynamic characteristics of the surrounding gas such as gas composition and pressure. Measurement of the resistor's phase delay in the thermal domain will thus provide information about gas composition and pressure. The Joule heating [30] comes from a periodically modulated electrical excitation, wherein the electrical excitation is modulated in time with a periodic electrical signal. The periodic electrical signal may be a sinusoidal signal, a square signal, a binary signal, a pulsed signal or any bounded periodic signal. The gas sensing method consists of measuring the phase delay (or time delay) between the thermal response of the variable electrical resistor and the modulated electrical excitation; wherein the phase delay (or the time delay) provides a measurement of the thermal capacity and thermal conductivity of the surrounding gas, both being related to gas composition and pressure as described previously.

The method for gas sensing herein described in this invention consists of heating the variable resistor [100] with a modulated electrical excitation [30], at a given modulation frequency, and of measuring its dynamic thermal response. The thermal response exhibits a phase delay (or, equivalently, a time delay) due to the thermal constants of the variable electrical resistor. Specifically, the time delay is related to the thermal dissipation mechanisms of the variable electrical resistor [40] [50] [60] [70] [80] which are related to gas composition and pressure. The time delay is also related to the thermal excitations [10] [20] [30] assumed to be dominated by the Joule heating $P_{elec}$ [30]. Taking into account the thermodynamic interactions between the variable electrical resistor [100] and its surroundings [300] [400], the following heat equation can be derived:

$$C\frac{d(\Delta T)}{dt} + G(\Delta T) = P_{elec} = P + \frac{dP}{dT}\Delta T + P_o\exp(j\omega t).$$

Where C is the thermal capacity of the variable electrical resistor [100], G its coefficient of thermal conduction comprising every heat dissipation mechanisms previously defined, and $\Delta T$ the temperature change of the variable electrical resistor [100] with respect to the substrate [300]: $\Delta T=T_b-T_s$. The right hand side of the equation represents the electrical power applied to the variable electrical resistor [30]. The applied electrical power $P_{elec}$ [30] consists of an instantaneous power P at t=0 that may change by an amount (dP/dT)$\Delta T$ with respect to a change of temperature $\Delta T$ at t>0 due to the presence of temperature-dependent electrical resistances in the readout electrical circuit, and of a modulated power component of amplitude $P_o$ at the modulation frequency $\omega$. Assuming that C and G are not strongly dependent on temperature, the solution to the change of temperature $\Delta T$ of the variable electrical resistor [100] with respect to the temperature of the substrate [300] $T_s$ is:

$$\Delta T = \frac{P}{G}\left(1 - \exp\left(\frac{G}{C}t\right)\right) + \frac{P_o\exp(j\omega t)}{G + j\omega C}$$

Where: $G=G_{leg}+G_{radiation}+G_{gas}+G_{conv}-dP/dT$.

The first term of the solution on $\Delta T$ represents a transient that becomes stable after a time t>C/G which is typically 100 msec or more. The second term is a steady-state periodic function. The term dP/dT is the differential Joulean heating of the readout circuit which is assumed to be constant within the $\Delta T$ range of interest. Let's consider only the steady-state regime:

$$\Delta T = \frac{P}{G} + \frac{P_o\exp(j\omega t)}{G + j\omega C} = \frac{P}{G} + \frac{P_o\exp(j\omega(t-t_o))}{(G^2+\omega^2 C^2)^{1/2}}$$

Since the electrical resistance $R_b$ of the variable electrical resistor [100] is function of temperature, by virtue of its non-zero Temperature Coefficient of Resistance (TCR), there will be periodic modulation of the electrical resistance $R_b$ at steady-state:

$$R_b = R_{bo}(1+\alpha\Delta T) = R_{bo}\left(1 + \alpha\frac{P}{G} + \alpha\frac{P_o\exp(j\omega(t-t_o))}{(G^2+\omega^2 C^2)^{1/2}}\right)$$

Where $\alpha$ is the temperature coefficient of resistance (TCR) of the variable electrical resistor [100] and $R_{bo}$ its electrical resistance at the reference substrate temperature $T_b=T_s$. In the present invention, it is desirable to have as large a TCR as possible for the variable electrical resistor in order to magnify the modulation of its electrical resistance, and therefore improve device sensitivity. Ideally, the TCR should be larger than 0.5% per Kelvin ($\alpha$>0.005). Therefore, the resistor [100] acts as a variable electrical resistance due to its non-zero TCR, and both its temperature $T_b$ and time delay $t_o$ can be determined by monitoring the periodic modulation of $R_b$ at steady-state.

The time delay $t_o$ between the electrical excitation [30] and the thermal response of the variable electrical resistor [100] is given by:

$t_o=a\tan[\omega C/G]/\omega=a\tan[\omega(C_1+C_2p)/(G_{leg}+G_{radiation}+G_{gas}+G_{conv}-dP/dT)]/\omega$ Where C and G are related to gas composition and pressure as described previously. Since the electrical excitation is modulated at a frequency $\omega$, the time delay $t_o$ corresponds to a phase delay (or phase delay) $\phi=\omega t_o$ between the electrical excitation [30] and the thermal response of the variable electrical resistor [100], given by:

$\phi=\omega t_o=a\tan[\omega C/G]=a\tan[\omega(C_1+C_2p)/(G_{leg}+G_{radiation}+G_{gas}+G_{conv}-dP/dT)]$.

Time delay and phase delay are both related to the thermal capacity C and thermal conductivity G of the variable electrical resistor. Therefore a measurement of time delay $t_o$, or phase delay $\phi$, by monitoring the periodic modulation of the resistor electrical resistance $R_b$ at steady-state will provide a measurement of C and G of the variable electrical resistor [100]. Since C and G depend on gas composition and gas pressure p within the environment as mentioned previously, a measurement of time delay $t_o$, or phase delay $\phi$, will procure a measurement of gas composition or of gas pressure p within the environment. The differential Joulean heating term dP/dT depends on the specifics of the readout circuit and is known for a given readout circuit with known resistances.

Figure 3:
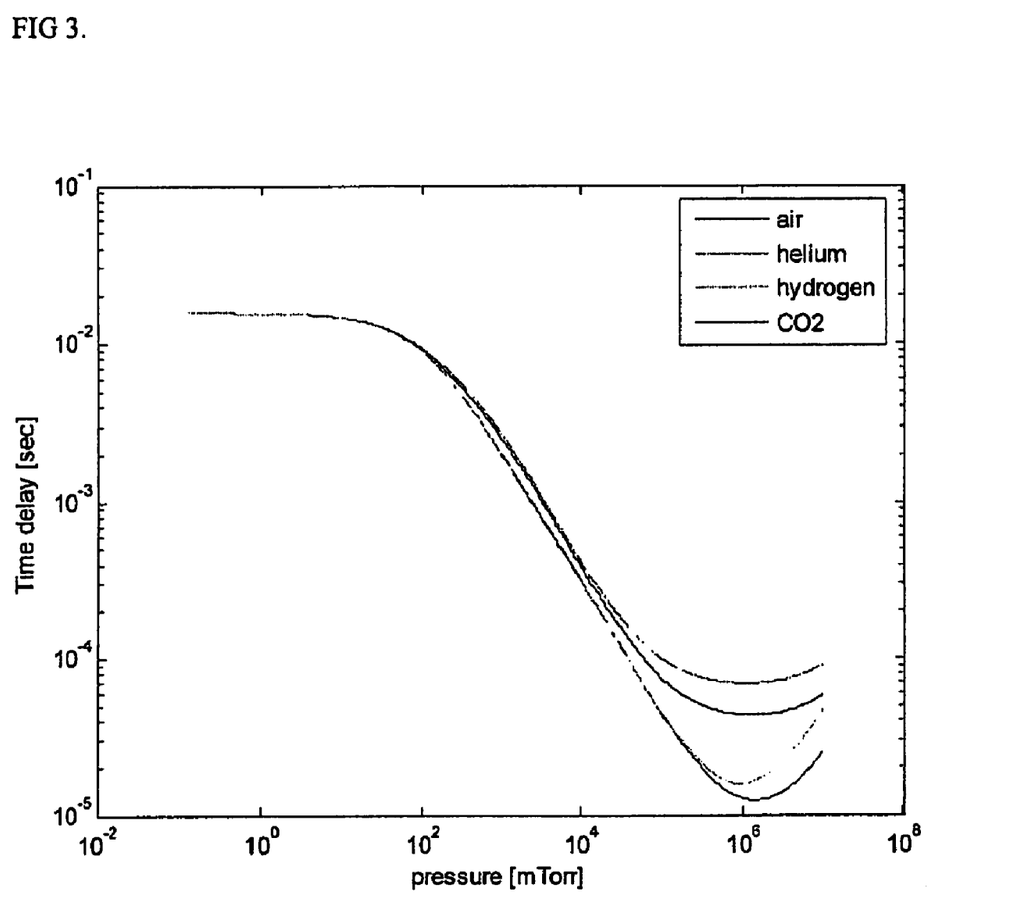
FIG. 3. shows the variation of time delay $t_o$ as a function of air pressure p, for a 35×35 um$^2$ variable electrical resistor gas pressure sensor at small modulation frequency $\omega$.

FIG. 3 plots the relation between time delay $t_o$ and gas pressure p for an exemplary variable electrical resistor 35 μm in size. The plot assumes negligible differential Joulean heating. It can be seen that the time delay $t_o$ varies between 0.01 msec and 100 msec as function of pressure p in the range of gas pressures between $10^{-4}$ Torr and $10^4$ Torr. Therefore, gas pressure measurement can be performed in real time over a wide pressure range with less than 100 msec between each measurement. Also, it can be seen that the time delay $t_o$ varies according to gas composition. Discrimination between different gas compositions is best obtained at pressures above 10 Torr. Therefore, gas composition measurement can be performed in real time with less than 1 msec between each measurement at a given gas pressure p in the range between $10^2$ Torr and $10^5$ Torr. A single measurement of time delay $t_o$ can provide either a gas pressure measurement or a gas composition measurement, not both at the same time.

Since C and G are both positive, the phase delay $\phi=\omega t_o$ will range between 0 and $\pi/2$ for all pressure ranges. Generally, depending on the thermal capacity C of the variable electrical resistor device, an appropriate electrical excitation modulation frequency is between 1 Hertz and $10^5$ Hertz. The inflection point near $10^3$ Torr in the time-delay curve generally limits the measurement pressure range from $10^{-4}$ Torr to $10^3$ Torr. The variable electrical resistor sensor of the present invention can thus be used to monitor the pressure of a gas below and at atmospheric pressure, so the sensor is not limited to sensing gas pressure inside vacuum environments or packages. By a proper design of the distance $d_s$ between the variable electrical resistor [100] and the substrate [300], of the distance $d_e$ between the variable electrical resistor [100] and the window [500], of the surface area A and emissivity ε of the variable electrical resistor [100], of the length of the suspending legs [200] and of the variable electrical resistor temperature $T_b$, etc., the gas pressure sensing capability of the variable electrical resistor gas sensor can be tuned below $10^{-4}$ Torr or above $10^3$ Torr. Low pressure sensing capability can be achieved, for example, by increasing the surface area A and decreasing the emissivity ε of the variable electrical resistor [100] and by increasing the length of the suspending legs [200]. High pressure sensing capability can be achieved, for example, by decreasing the distances $d_s$ and $d_e$ between the variable electrical resistor [100] and the substrate [300] and window [500]. Gas pressure sensing tuning capabilities of the variable electrical resistor gas sensor are not limited to these specific parameter changes. Several variable electrical resistors, with different physical characteristics such as the ones just mentioned, may be combined within a single readout circuit to provide sensing capability over a wider dynamic range than a single variable electrical resistor. For example, several variable electrical resistors may be combined and tuned for measuring gas pressure at low pressure regimes, while several other variable electrical resistors may be combined in the same readout circuit and tuned for measuring gas pressure at high pressure regimes; the plurality of variable electrical resistors thus combined to provide sensing capability over an overall wider dynamic range. The plurality of variable electrical resistors may be combined in series or in parallel with respect to the voltage source [120] along with load resistances, or load inductances, or load capacitances, or a combination thereof comprised in the same readout circuit [101].

Figure 4:
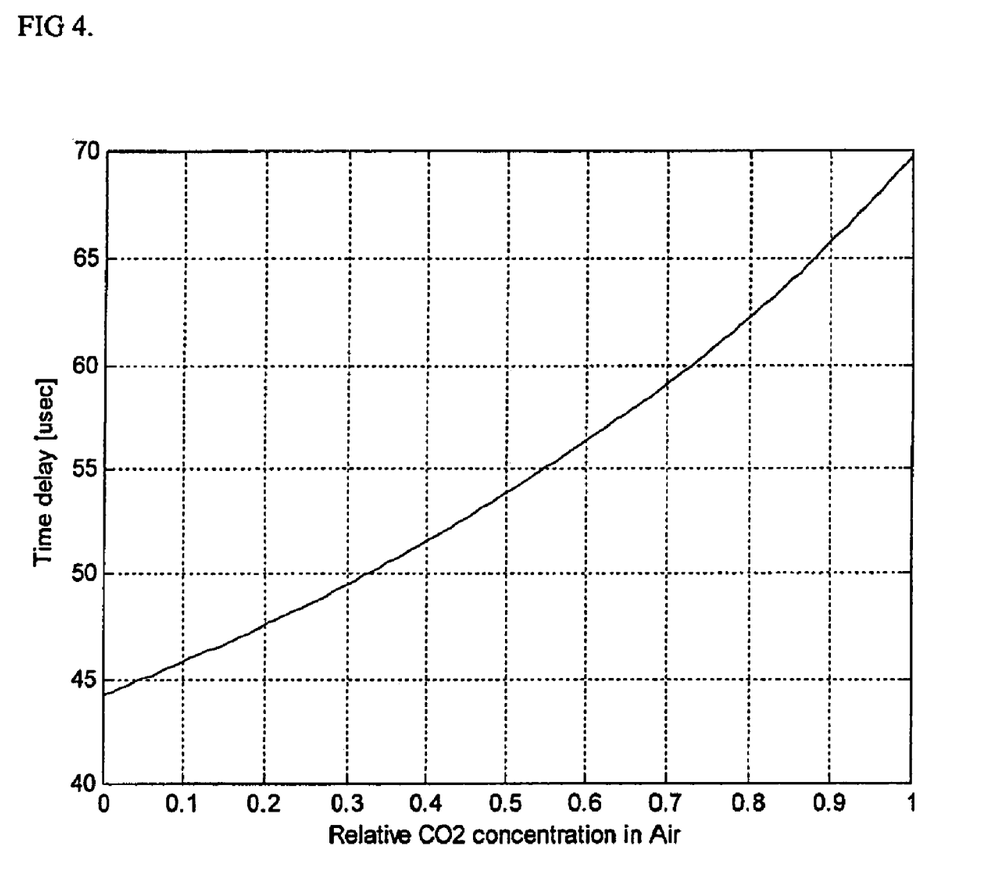
FIG. 4. shows a variation of time delay $t_o$ as a function of carbon dioxide ($CO_2$) concentration in air at atmospheric pressure, for a 35×35 um$^2$ variable electrical resistor gas pressure sensor at small modulation frequency $\omega$.

The same variable electrical resistor gas sensor, or plurality of variable electrical resistor gas sensors, can also be used for sensing gas composition. Gas composition measurements can be performed at a given gas pressure p in the range of pressures between $10^2$ Torr and $10^5$ Torr. FIG. 4 plots the relation between time delay $t_o$ and gas composition for an exemplary variable electrical resistor of 35 um in size. The plot assumes negligible differential Joulean heating. In this example, the relative concentration of $CO_2$ in Air at atmospheric pressure modifies significantly the time delay of the gas sensor, which can be used to determine gas composition as long as the nature of the gas mixture is known.

In this invention, the method for sensing gas with a variable electrical resistor is based on measuring the thermal response of the variable resistor with periodically modulated electrical excitations. The method consists of measuring the time delay (or phase delay) between the signal modulation of the variable electrical resistor [100] and the signal modulation of the electrical excitation [30] which acts as a reference signal. Since the time delay (or phase delay) is related to the thermal capacity and thermal conductivity of the variable electrical resistor, a measurement of gas composition or gas pressure within the environment is obtained as described previously.

Generally, the method for gas sensing herein described in the present invention consists of; 1) Electrically exciting a variable electrical resistor with a periodically modulated voltage source signal, wherein said variable electrical resistor changes electrical resistance with a change of temperature; and 2) Measuring the time delay between the signal modulation of the said periodically modulated voltage source and the signal modulation of the said variable electrical resistor; and 3) Determining gas pressure from said time delay; or 4) Determining gas composition from said time delay.

Figure 5:
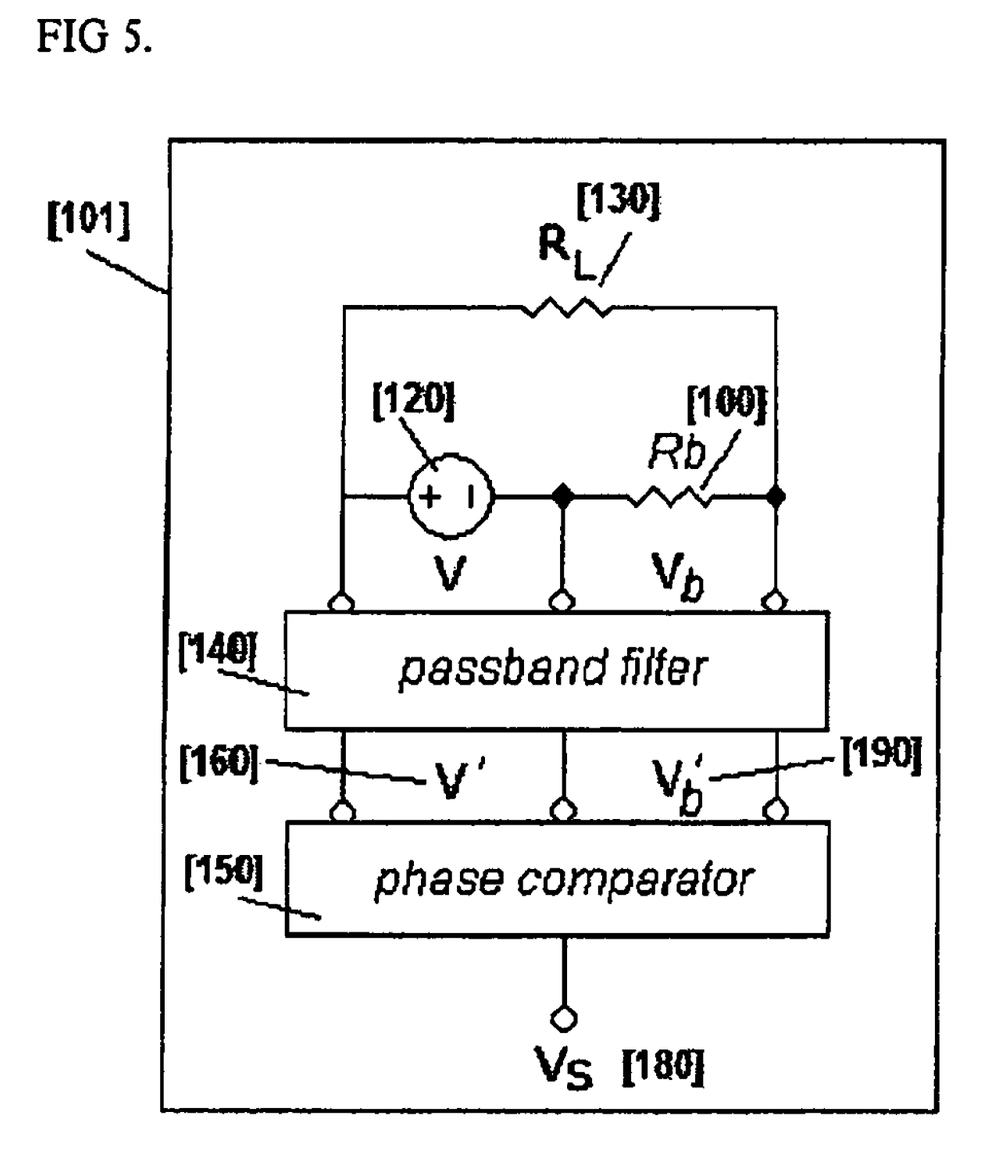
FIG. 5. shows an exemplary embodiment of the gas sensor assembly.

FIG. 5 schematizes an embodiment of a gas sensor assembly of the present invention. The gas sensor assembly of the present invention comprises: 1) At least one variable electrical resistor [100] proximal to a substrate [300] exposed to the gas pressure of a given atmospheric environment [400]; and 2) A readout electrical circuit [101] connected to the said variable electrical resistor [100], wherein said variable electrical resistor acts as a variable electrical resistance in the said readout electrical circuit; and 3) A periodically modulated voltage source [120] electrically connected to the said variable electrical resistor [100], wherein said periodically modulated voltage source is part of said readout electrical circuit [101]; and 4) A passband filter [140] electrically connected to a phase comparator [150].

The variable electrical resistor gas sensor assembly of the present invention generally refers to an assembly comprising the variable electrical resistor [100], suspending legs [200] and a substrate [300] all connected electrically to a readout electrical circuit [101]. The readout electrical circuit [101] of the present invention comprises the variable electrical resistor [100], the periodically modulated voltage source [120], the passband filter [140] and the phase comparator [150]. In addition, the readout electrical circuit [101] may comprise a plurality of load resistors, capacitors and inductors. The readout circuit may be integrated on the substrate [300] by CMOS fabrication process, or be external to the substrate and made of standard electronics components electrically connected to the variable electrical resistor [100]. The variable electrical resistor [100] is a variable electrical resistance whose electrical resistance is function of the temperature, is part of the readout circuit [101] and is exposed to the gas of a given atmospheric environment [400]. The rest of the readout circuit [101] may or may not be exposed to the gas of the environment [400]. The readout circuit [101] surface area may be as small as 1 mm² or smaller.

Complexity is introduced when the specifics of the readout circuit [101] are taken into account, in particular when the heat flow equation includes the differential Joulean heating due to a constant power bias at the variable electrical resistor [100]. A constant power bias appears when the circuit is driven with a periodically modulated voltage source $V=V(t,\omega)$. A preferred embodiment consists of a digital readout circuit where the voltage source [120] generates a periodic binary signal of alternating ones and zeros of voltage amplitude $\Delta v$ described by the summation of several Fourier components of frequency harmonic n:

$$v(t,\omega) = \Delta v Rect(t,\omega) = \Delta v \left( 0.5 + \frac{1}{\pi} \sum_{n=\pm 1,3,5...}^{\pm \omega} \frac{1}{|n|} \exp(jn\omega t) \right)$$

Considering the embodiment shown in FIG. 5, the instantaneous power dissipated at the variable electrical resistor [100] is given by the following transfer function:

$$P_b = R_{bo} i_b^2 = \Delta v^2 Rect^2(t,\omega) R_{bo}/(R_L+R_{bo})^2 = \Delta v^2 Rect(t,\omega) R_{bo}/(R_L+R_{bo})^2.$$

The advantages of using the abovementioned periodic binary signal $V(t,\omega)$ are 1) its compatibility with digital circuits and 2) its spectral invariance when the voltage source is raised to the $2^{nd}$ power. The later specifies that when the voltage source is modulated with a periodic binary signal with a spectral content of $V\sim\exp(jn\omega t)$, the resistance is also modulated with the same spectral content as the voltage source, $R_b\sim\exp(jn\omega t)$. The present invention is not limited to periodic binary signal voltage sources; other periodic functions, such as raised periodic square signals, raised periodic sinusoidal signals, raised periodic triangular signals or raised periodic pulsed signals, may show the same advantages than the abovementioned periodic binary signal.

For the embodiment shown in FIG. 5, the solutions for $\Delta T$ and $R_b$ at steady-state will be of the form:

$$\Delta T = \frac{\Delta v^2 R_{bo}}{4G(R_L+R_{bo})^2} + \frac{\Delta v^2 R_{bo}}{(R_L+R_{bo})^2} \left( \frac{1}{\pi} \sum_{n=\pm 1,3,5...}^{\pm \omega} \frac{1}{|n|} \frac{\exp(jn\omega t)}{G+j|n|\omega C} \right)$$

$$R_b = R_{bo} \left( 1 + \alpha \frac{\Delta v^2 R_{bo}}{4G(R_L+R_{bo})^2} + \alpha \frac{\Delta v^2 R_{bo}}{(R_L+R_{bo})^2} \left( \frac{1}{\pi} \sum_{n=\pm 1,3,5...}^{\pm \omega} \frac{1}{|n|} \frac{\exp(jn\omega t)}{G+j|n|\omega C} \right) \right)$$

Where:

$$G=G_{leg}+G_{radiation}+G_{gas}+G_{conv}-\alpha\Delta v^2 R_{bo}(R_L-R_{bo})/2(R_L+R_{bo})^3.$$

These solutions for $\Delta T$ and $R_b$ are valid in the regime of small $\Delta T$ of only a few degrees Kelvin where any non-linear thermal variations of electrical resistance can be neglected. Thus, when the readout circuit is driven with a modulated periodic voltage source $V=V(t,\omega)$ [120], the thermal conductivity of the variable electrical resistor [100] is changed to an "effective G" comprising the resistor differential Joulean heating $dP_b/dT=\alpha R_b dP_b/dR_b$.

The circuit can be driven by a modulated voltage source [120] with periodic binary signal of alternating ones and zeros of fundamental frequency $\omega=\omega_o$ (i.e. $n=\pm 1$), and the load voltage can be filtered by a passband filter [140] transmitting signals at the frequency $\omega=\omega_o$ and blocking signals at other frequency harmonics $|n|>1$. The passband filter [140] may consist of a RC, or RL, or RCL analog or digital electronic filter. Under such modulation conditions, it can be shown that the electrical resistance $R_b$ of the variable electrical resistor [100] exhibits a time-delayed modulation component at the fundamental frequency $\omega=\omega_o$:

$$R_{0(n=\pm 1)} = \frac{2\alpha\Delta v^2 R_{bo}^2}{\pi(R_L+R_{bo})^2} \frac{\cos(\omega_o t)}{G+j\omega_o C}$$

$$= \frac{2\alpha\Delta v^2 R_{bo}^2}{\pi(R_L+R_{bo})^2} \frac{\cos(\omega_o(t-t_s))}{(G^2+\omega_o^2 C^2)^{1/2}}$$

At the fundamental frequency $\omega=\omega_o$ (i.e. $n=\pm 1$) the time delay $t_o$ of the electrical resistance $R_b$ [100] is given by:

$$n\omega C/\tan(\omega t_o)=\omega_o C/\tan(\omega_o t_o)=G_{leg}+G_{radiation}+G_{gas}+G_{conv}-\alpha\Delta v^2 R_{bo}(R_L-R_{bo})/2(R_L+R_{bo})^3$$

Time delay measurements can also be obtained at other frequency harmonics $|n|>1$ with a passband filter [140] transmitting at the frequency $\omega=n\omega_o$. The specifics of the readout circuit, comprising resistances, capacitances and inductances, may include an additional circuit-related phase delay from 0 to $2\pi$, which is known and taken into account during sensor calibration.

FIG. 5 shows an exemplary readout circuit embodiment of the invention. The readout circuit [101] includes a modulated voltage source [120] driving both a variable electrical resistor [100] and a load resistance [130]. The readout circuit [101] also includes an electrical passband filter [140] connected to an electrical phase comparator [150]. The voltage $V_b$ at the variable electrical resistor [100] is connected to the passband filter [140]. The readout circuit [101] may be made of analog or digital electronics components or a combination of analog and digital electronics components. Given this circuit embodiment, the voltage $V_b$ at the variable electrical resistor [100] is given by the following transfer function well known in the art:

$$V_b=VR_b/(R_L+R_b)$$

Consequently, the voltage $V_b$ will exhibit time-delayed modulation since $V_b$ is related to the time-delayed $R_b$ by virtue of the abovementioned transfer function. The time delay $t_{ob}$ between the voltage V and the voltage $V_b$ may be different than the abovementioned time delay $t_o$ between the voltage V and the electrical resistance $R_b$ [100] since $V_b$ and $R_b$ scale differently with respect to V. For instance, the ratio between $R_L$ and $R_b$ will determine the value of the time delay $t_{ob}$ between the voltage V and the voltage $V_b$, and the time delay $t_{ob}$ will converge to the value $t_o$ under the condition $R_b \gg R_L$. The modulated voltage source V and the resistor voltage $V_b$ are connected to a passband filter [140] and a phase comparator [150], wherein the voltage source V acts as a reference signal with a time delay of zero. The phase comparator [150] provides an electrical output voltage proportional to the difference of phase between V and $V_b$: $V_s \sim \omega_o t_{ob}$, wherein a calibration curve between the time delay $t_{ob}$ and gas pressure p can be determined.

Since the time delay (or phase delay) is related to gas pressure as described previously, the gas pressure can be determined by the output voltage $V_s$ [180] of the phase comparator [150] of the readout circuit [101]. Also, since the time delay (or phase delay) is related to gas composition as described previously, the gas composition can be determined by the output voltage $V_s$ [180] of the phase comparator [150] of the readout circuit [101]. The phase comparator [150] may consist of a X-OR digital element combined with an integrator, a voltage combiner element combined with an integrator, or any component that provides frequency and phase analysis such as a Fourier analysis apparatus.

The invention is not limited to this specific readout circuit embodiment and may show different circuit architectures comprising electrical resistors, capacitors and inductors, connected in such a way as to generate different transfer functions with or without electrical gain, and utilized to provide a measurement of the time delay of the variable electrical resistor [100], wherein the voltage source V [120] acts as a reference signal to the phase comparator [150].

The gas sensor assembly of the present invention becomes calibrated for gas pressure measurements by specifying the parametric relation between the output voltage $V_s$ [180] of the phase comparator and the gas pressure p within the environment [400]. The relation between $V_s$ and p for the gas sensor assembly is given by a parametric relation. Assuming no temperature dependence, the relation between $V_s$ and p, and the relation between $t_o$ and p, are fundamentally linked to the relation between the thermal capacity C and the thermal conductivity G of the variable electrical resistor and the gas pressure p:

$$\frac{\beta \cdot A}{\frac{ds}{\lambda_{gas_s}} + \frac{1}{\gamma_{gas} \cdot p}} + \frac{k \cdot \beta \cdot A}{\frac{de}{\lambda_{gas_e}} + \frac{1}{\gamma_{gas} \cdot p}} + G_{leg} + G_{radiation} + G_{conv} - \frac{dP}{dT} = \frac{\omega(C_1 + C_2 p)}{\tan(\omega t_o)}$$

This transfer function can be reduced to a 6-parameter polynomial relation relating pressure p with time delay $t_o$ that cancels the need for precise knowledge of the parameters of the system ($\lambda_{gas\_s}$, $\lambda_{gas\_e}$, $\gamma_{gas}$, $\alpha$, $\eta$, $T_s$, $T_{env}$, $\epsilon$, $d_s$, $d_e$, $\beta$, h, $C_1$, $C_2$, $R_L$, etc.). The following polynomial relation is valid for variable electrical resistors [100] having a platform, wire or coil geometry:

$$\frac{1}{(1 + X6p)}\left(X1 + \frac{X2}{(X3 + p^{-1})} + \frac{X4}{(X5 + p^{-1})}\right) = \frac{\omega}{\tan(\omega t_o)}$$

Therefore, calibrating the gas sensor assembly made of a variable electrical resistor [100] and readout circuit [101] requires at least 6 parameters, because the mathematical relation between gas pressure and time delay comprises at least 6 parameters; X1, X2, X3, X4, X5 and X6. These parameters can be measured by performing at least 6 time delay (or phase delay, or phase comparator output voltage) measurements at a specific modulation frequency ω and at least 6 different gas pressures, from which the parameters can be determined using standard fitting routines. These parameters depend on several factors such as temperature, gas composition and variable electrical resistor physical characteristics. A single parametric relation can be applied to a plurality of gas sensor assemblies if factors such as temperature, gas composition and variable electrical resistor physical characteristics are kept the same. Therefore, if the temperature and gas composition are constant, the same parametric relation applies to a plurality of gas sensor assemblies of the same physical characteristics. Measurements and calibration should always be done at a specific modulation frequency ω.

Also, the gas sensor assembly of the present invention becomes calibrated for gas composition measurements by specifying the parametric relation between the output voltage $V_s$ [180] of the phase comparator and the gas composition within the environment [400]. The gas composition determines the values of $\lambda_{gas}$, $\gamma_{gas}$, and $C_2$. Therefore only parameters X2, X3, X4, X5 and X6 have to be calibrated with respect to gas composition, and the same abovementioned mathematical parametric relation can be used for calibrating the gas sensor assembly for gas composition measurements.

While this invention has been particularly shown and described with references to preferred embodiments thereof, it will be understood by those skilled in the art that various changes in form and details may be made therein without departing from the scope of the invention encompassed by the appended claims.

The invention claimed is:

1. A method for sensing gas comprising:
   providing a variable electrical resistor in a gas environment, said variable electrical resistor changing electrical resistance with a change of temperature;
   electrically exciting said variable electrical resistor with a periodically modulated voltage source signal;
   measuring a time delay between the signal modulation of said periodically modulated voltage source and the signal modulation of said variable electrical resistor; and
   determining gas pressure from said time delay; or
   determining gas composition from said time delay, said gas pressure or said gas composition being determined from a mathematical parameter relation.

2. The method for gas sensing of claim 1 wherein the same mathematical parametric relation can be used for said determination of gas pressure and said determination of gas composition.

3. The method for gas sensing of claim 1 wherein said time delay is related to the thermal capacity and the thermal conductivity of said variable electrical resistor.

4. The method for gas sensing of claim 1 wherein said time delay applies to a plurality of variable electrical resistors of the same physical characteristics.

5. The method for gas sensing of claim 1 wherein said time delay is related to a phase delay.

6. The method for gas sensing of claim 1 wherein the said periodically modulated voltage is a periodic sinusoidal signal, a periodic square signal, a periodic binary signal, a periodic triangular signal, or a periodic pulsed signal.

7. The method for gas sensing of claim 1 wherein said periodically modulated voltage has a fundamental frequency between 1 Hertz and $10^5$ Hertz.

8. The method for gas sensing of claim 1 wherein said measurement of time delay is done in real time, with less than 100 milliseconds between each measurement.

9. A gas sensor assembly comprising:
   at least one variable electrical resistor proximal to a substrate, exposed to the gas pressure of a given atmospheric environment;
   an electrical readout circuit connected to said variable electrical resistor, said variable electrical resistor acting as a variable electrical resistance in said electrical readout circuit;
   a periodically modulated voltage source electrically connected to said variable electrical resistor, wherein said periodically modulated voltage source is part of said readout electrical circuit; and a passband filter electrically connected to a phase comparator.

10. A gas sensor assembly according to claim 9 wherein said variable electrical resistor is a micro-thermistor.

11. A gas sensor assembly according to claim 9 wherein said variable electrical resistor is a suspended-platform MEMS device.

12. A gas sensor assembly according to claim 9 wherein said variable electrical resistor is a suspended wire.

13. A gas pressure sensor according to claim 9 wherein said variable electrical resistor has a width and a length between 0.1 μm and 1000 μm.

14. A gas pressure sensor assembly according to claim 9 wherein said variable electrical resistor has a thermal conductivity and a thermal capacity that vary in response to a change in gas pressure.

15. A gas pressure sensor assembly according to claim 9 wherein said variable electrical resistor has a thermal conductivity and thermal capacity that vary in response to a change in gas composition.

16. A gas pressure sensor assembly according to claim 9 wherein said variable electrical resistor is made of a material with a Temperature Coefficient of Resistance (TCR) of at least 0.5% per Kelvin.

17. A gas pressure sensor assembly according to claim 9 wherein said variable electrical resistor is made with vanadium oxide.

18. A gas pressure sensor assembly according to claim 9 wherein said variable electrical resistor is made with amorphous silicon.

19. A gas pressure sensor assembly according to claim 9 wherein said gas is air.

20. A gas pressure sensor assembly according to claim 9 wherein said gas is a mixture of several gases.

21. A gas pressure sensor assembly according to claim 9 wherein said gas pressure is between $10^{-4}$ to $10^5$ Torr.

22. A gas pressure sensor assembly according to claim 9 wherein the electrical readout circuit is analog or digital.

23. A gas pressure sensor assembly according to claim 9 wherein said electrical readout circuit comprises a plurality of said variable electrical resistors.

24. A gas pressure sensor assembly according to claim 9 wherein said substrate is a CMOS device.

25. A gas pressure sensor assembly according to claim 9 wherein said passband filter is a RC, or RL, or RCL electronic circuit.

26. A gas pressure sensor assembly according to claim 9 wherein said phase comparator is analog or digital.

27. A gas pressure sensor assembly according to claim 9 wherein said phase comparator is an X—OR digital element combined with an integrator.

28. A gas pressure sensor assembly according to claim 9 wherein said phase comparator is a voltage combiner element combined with an integrator.

* * * * *